(12) United States Patent
Chelak et al.

(10) Patent No.: US 12,239,812 B2
(45) Date of Patent: Mar. 4, 2025

(54) UNITARY MEDICAL CONNECTOR

(71) Applicant: NP Medical Inc., Clinton, MA (US)

(72) Inventors: Todd Chelak, Pelham, NH (US); Luis Maseda, Natick, MA (US)

(73) Assignee: NP Medical Inc., Clinton, MA (US)

( * ) Notice: Subject to any disclaimer, the term of this patent is extended or adjusted under 35 U.S.C. 154(b) by 273 days.

(21) Appl. No.: 17/984,456

(22) Filed: Nov. 10, 2022

(65) Prior Publication Data
US 2023/0074383 A1 Mar. 9, 2023

Related U.S. Application Data

(63) Continuation of application No. 16/083,779, filed as application No. PCT/US2017/021529 on Mar. 9, 2017, now Pat. No. 11,524,149.

(60) Provisional application No. 62/306,241, filed on Mar. 10, 2016.

(51) Int. Cl.
B29C 67/00 (2017.01)
A61M 39/04 (2006.01)
A61M 39/26 (2006.01)
B29C 64/106 (2017.01)
B33Y 80/00 (2015.01)

(52) U.S. Cl.
CPC .......... *A61M 39/045* (2013.01); *A61M 39/26* (2013.01); *B29C 64/106* (2017.08); *B33Y 80/00* (2014.12); *A61M 2207/00* (2013.01)

(58) Field of Classification Search
CPC ........ B29C 64/106; B33Y 10/00; B33Y 80/00
See application file for complete search history.

(56) References Cited

U.S. PATENT DOCUMENTS

| 5,167,648 A | 12/1992 | Jepson et al. |
|---|---|---|
| 8,512,294 B2 | 8/2013 | Ou-Yang et al. |
| 2005/0178462 A1 | 8/2005 | Py |
| 2010/0030164 A1 | 2/2010 | Kimball et al. |
| 2015/0126942 A1 | 5/2015 | Lopez et al. |
| 2016/0074866 A1 | 3/2016 | Stokes et al. |
| 2019/0070400 A1 | 3/2019 | Chelak et al. |

FOREIGN PATENT DOCUMENTS

WO    2009/148577 A1    12/2009

OTHER PUBLICATIONS

U.S. Appl. No. 16/083,779, filed Sep. 10, 2018, 2019/0070400, Allowed.
International Search Report and Written Opinion for Application No. PCT/US2017/021529, dated May 19, 2017, 12 pages.

*Primary Examiner* — Thu Khanh T. Nguyen
(74) *Attorney, Agent, or Firm* — McCarter & English, LLP; Jonathan C. Lovely

(57) ABSTRACT

A one-piece medical connector has a unitary body. The unitary body includes a rigid portion that forms a housing. The unitary body also includes a resilient portion located at least partially within the housing. At least a movable portion of the resilient portion is configured to move relative to the rigid portion. Movement of the resilient portion selectively permits fluid flow through the connector. The rigid portion and the resilient portion form a one-piece unitary connector.

19 Claims, 8 Drawing Sheets

UNITARY MEDICAL CONNECTOR

PRIORITY

This application is a continuation of and claims priority from U.S. application Ser. No. 16/083,779, filed Sep. 10, 2018, entitled "Unitary Medical Connector with a Rigid and a Resilient Portion," assigned, now U.S. Pat. No. 11,524,149 B2, and naming Todd Chelak and Luis Maseda as inventors, the disclosure of which is incorporated herein, in its entirety, by reference.

U.S. application Ser. No. 16/083,779, in turn, is a 35 U.S.C. § 371 national stage filing of International Application No. PCT/US2017/021529, entitled "Unitary Medical Connector," filed on Mar. 9, 2017, and naming Todd Chelak and Luis Maseda as inventors, the disclosure of which is incorporated herein, in its entirety, by reference.

International Application No. PCT/US2017/021529 claims priority from United States Provisional Patent Application No. 62/306,241, filed Mar. 10, 2016, entitled "UNITARY MEDICAL CONNECTOR," and naming Todd Chelak and Luis Maseda as inventors, the disclosure of which is incorporated herein, in its entirety, by reference.

FIELD OF THE INVENTION

The invention generally relates to medical connectors and, more particularly, the invention relates to connectors made as a single piece.

BACKGROUND OF THE INVENTION

In general terms, medical connectors, such as valving devices, often act as a port that may be repeatedly accessed to non-invasively inject fluid into (or withdraw fluid from) a patient's vasculature. Consequently, a medical connector permits the patient's vasculature to be freely accessed without requiring the patient's skin be repeatedly pierced by a needle. Alternatively, medical connectors may act as a port for other medical applications, such as for accessing fluid containers (e.g. bags, vials), trachea tubes, enteral lines, breathing apparatuses, surgical sites, etc.

Medical personnel insert a medical instrument into the medical connector to inject fluid into (or withdraw fluid from) a patient who has an appropriately secured medical connector. Once inserted, fluid may be freely injected into or withdrawn from the patient.

SUMMARY OF VARIOUS EMBODIMENTS

In accordance with one embodiment of the invention, a one-piece medical connector has a unitary body. The unitary body includes a rigid portion that forms a housing. The unitary body may also include a resilient portion at least partially within the housing. At least a movable portion of the resilient portion may be configured to move relative to the rigid portion. Movement of the resilient portion may selectively permit fluid flow through the connector. The rigid portion and the resilient portion may form a one-piece unitary connector.

The resilient portion may be configured to deform upon insertion of a medical implement into the connector to transition from a closed mode to an open mode. Additionally, or alternatively, the movable part of the resilient portion may move so that the connector is in an open mode when exposed to a cracking pressure. The cracking pressures may be a proximally directed cracking pressure, or a distally directed cracking pressure. The proximally directed cracking pressure and the distally directed cracking pressure may be different. To that end, the medical connector may be formed from more than one material along a material divide line. For example, the resilient portion and/or the rigid portion may be formed from more than one material along a material divide line.

The connector may be a pressure-activated connector, or a luer-activated connector. Furthermore, the medical connector may be formed by additive manufacturing. For example, the rigid portion and the resilient portion may be formed by additive manufacturing, and the resilient portion may be formed to have a normally closed aperture. Specifically, the medical connector may be formed by 3D printing. At least a portion of the unitary medical connector may be formed as a material blend. The blend may be a homogeneous material blend, a ratio transition blend, and/or an instantaneous transition blend.

The housing of the medical connector may include a distal portion and a proximal portion. The proximal portion may form an inlet, while the distal portion may form an outlet. Alternatively, the proximal portion may form the outlet, and the distal portion may form the inlet. Furthermore, the housing may form an interior with a post member within the interior. The post member may include a lumen that is a part of the flow path of the medical connector, and the lumen may have a solid wall that surrounds and defines the lumen. The lumen may open to the interior of the housing.

In accordance with another illustrative embodiment, a method produces a medical connector. The method causes an additive printing device to print the medical connector according to a prescribed printing process, and the printing process has prescribed parameters. The medical connector may have a rigid portion forming a housing. The medical connector may also have a resilient portion that is internal to the housing, and the resilient portion and the rigid portion form a one-piece unitary housing. However, the resilient portion may be configured to move relative to the rigid portion, so that fluid flow is permitted in response to pressure.

The additive printing device used to produce the medical connector may include a 3D printer. The additive printing device may be able to print at least one material. Accordingly, the rigid portion may be formed from a first material and the resilient portion may be formed from a second material. The additive printing device may produce the connector in a plurality of layers according to the prescribed printing process.

In accordance with another illustrative embodiment, a one-piece medical connector has a unitary body. The body may be formed of a rigid portion formed as a single unitary connector with a resilient portion. The resilient portion may be configured to move relative to the rigid portion to selectively permit fluid flow through the medical connector. A transition portion formed of a material blend may be between the rigid portion and the resilient portion.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a medical connector (e.g., a medical valve) is formed as a one-piece unitary connector. The unitary connector may be 3D printed as a single piece. The connector includes a rigid portion forming a housing. The connector also includes a resilient portion, wherein at least a movable portion of the resilient portion is configured to move relative to the rigid portion to selectively permit fluid flow through the connector. Portions of the connector formed as a single piece may be formed from blends of different materials or different grades of material. Details of illustrative embodiments are discussed below.

Figure 1:
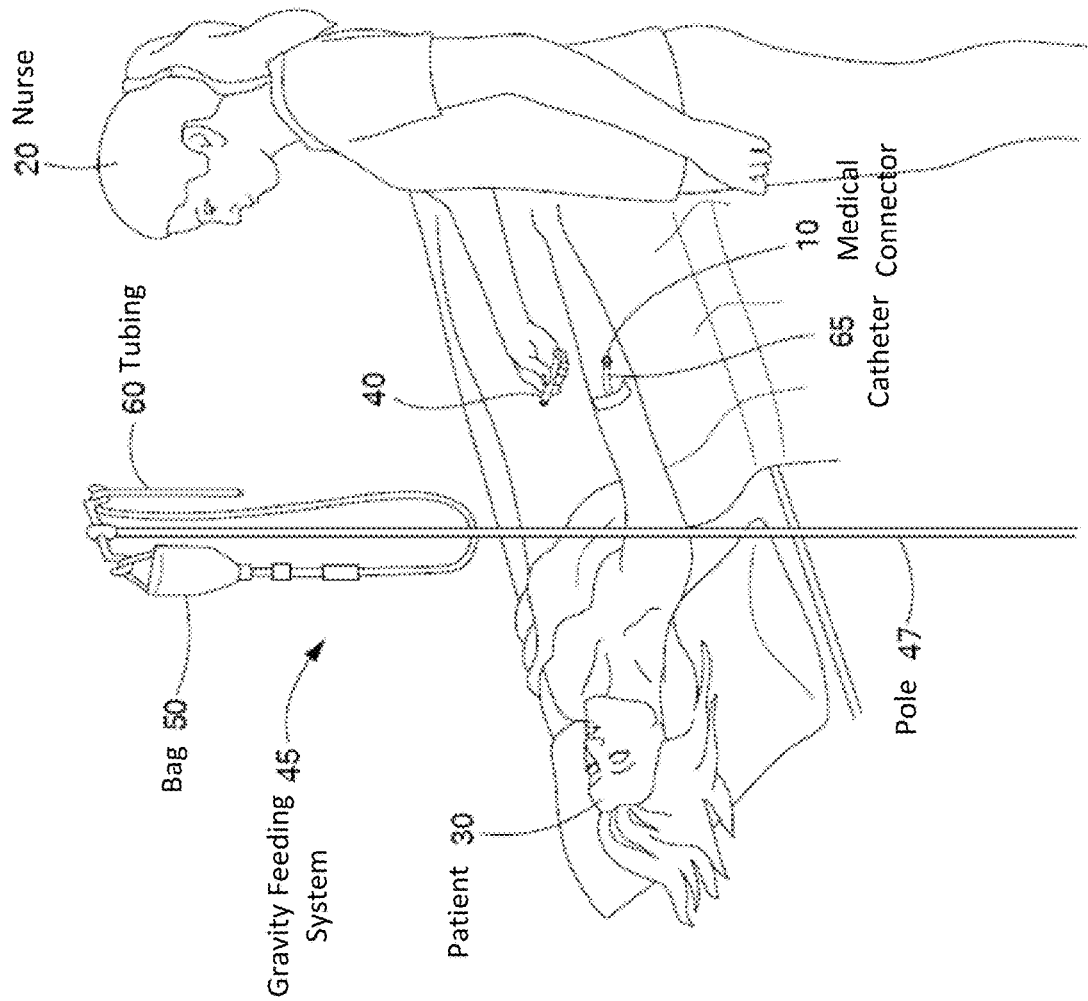
FIG. 1 schematically shows one use of a medical connector configured in accordance with illustrative embodiments of the present invention.

FIG. 1 schematically shows one illustrative use of a medical connector 10 configured in accordance with illustrative embodiments of the invention. In this example, a catheter 65 connects the connector 10 with a patient's vein (the patient is identified by reference number 30). Adhesive tape or similar material may be coupled with the catheter 65 and the patient's 30 arm to ensure that the connector 10 remains in place.

After the connector 10 is in place, a nurse, doctor, technician, practitioner, or other user (schematically identified by reference number 20) may intravenously deliver medication to the patient 30, who is lying in a hospital bed. To that end, after the connector 10 is properly primed and flushed (e.g., with a saline flush), the nurse 20 swabs the top surface of the connector 10 to remove contaminants. Next, the nurse 20 uses a medical instrument (e.g., a syringe having a distally located blunt, luer tip complying with ANSI/ISO standards) to inject medication into the patient 30 through the connector 10. For example, the medical practitioner 20 may use the connector 10 to inject drugs such as heparin, antibiotic, pain medication, other intravenous medication, or other fluid deemed medically appropriate. Alternatively, the nurse 20 (or other user) may withdraw blood from the patient 30 through the connector 10.

The medical connector 10 may receive medication or other fluids from other means, such as through a gravity feed system 45. In general, traditional gravity feeding systems 45 often have a bag 50 (or bottle) containing a fluid (e.g., anesthesia medication) to be introduced into the patient 30. The bag 50 (or bottle) typically hangs from a pole 47 to allow for gravity feeding. The medical practitioner 20 then connects the bag/bottle 50 to the medical connector 10 using tubing 60 having an attached blunt tip. In illustrative embodiments, the blunt tip of the tubing 60 has a luer taper that complies with the ANSI/ISO standard. After the tubing 60 is connected to the medical connector 10, gravity (or a pump) causes the fluid to begin flowing into the patient 30. In some embodiments, the feeding system 45 may include shut-off devices on the tubing 60 (e.g., stop-cocks or clamps) to stop fluid flow without having to disconnect the tubing 60 from the connector 10. Accordingly, the connector 10 can be used in long-term "indwell" procedures.

In other medical applications, alternative access procedures are performed by medical personnel 20 for accessing fluid containers (e.g. bags, vials), trachea tubes, enteral lines, breathing apparatuses, surgical sites, etc. through the medical connector 10.

Figure 2:
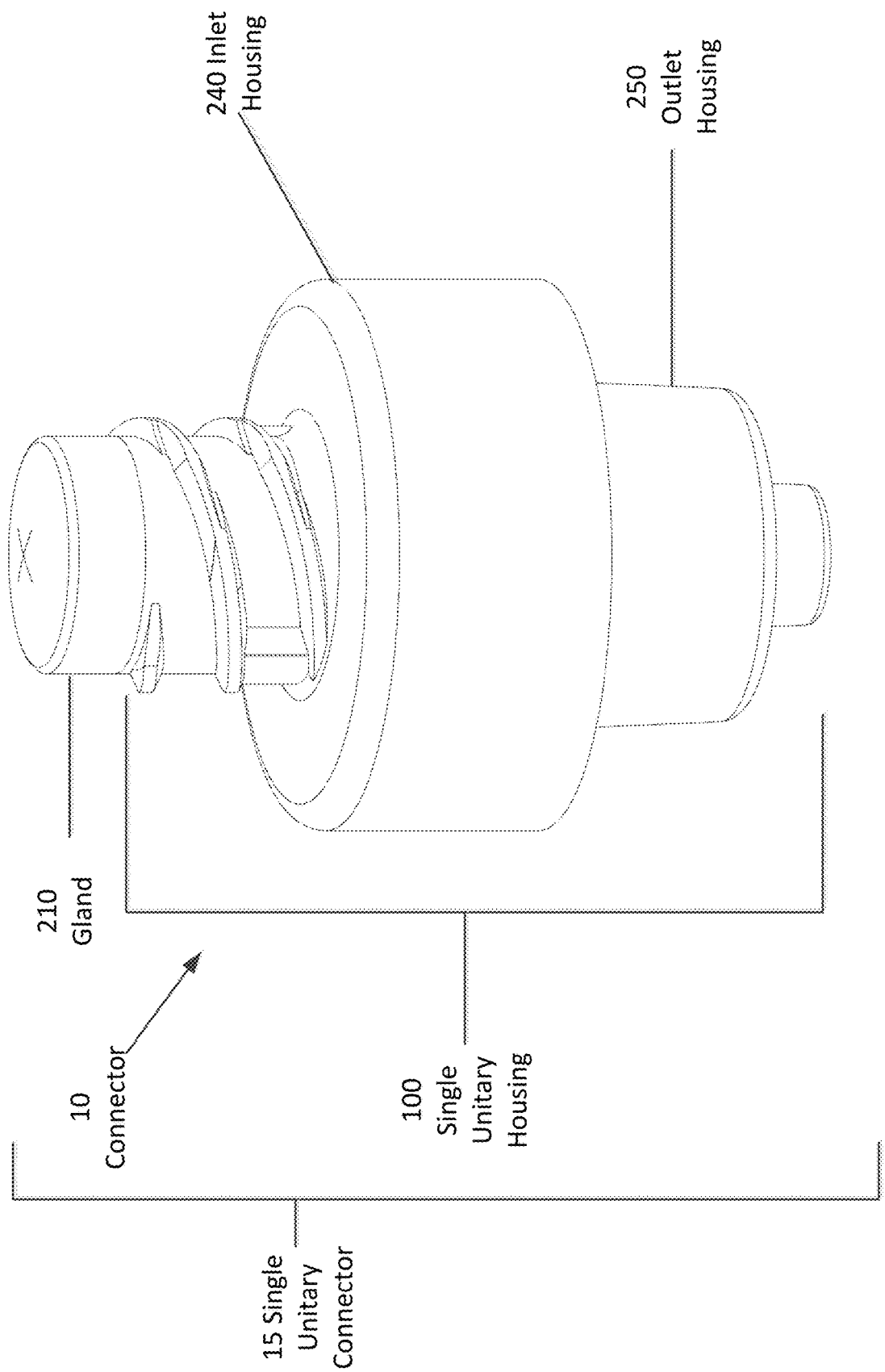
FIG. 2 schematically shows a perspective view of a unitary medical connector formed by an additive printing process in accordance with illustrative embodiments of the invention.

FIG. 2 schematically shows a perspective view of a unitary medical connector 10 in accordance with illustrative embodiments of the invention. From a manufacturing standpoint, it is desirable to reduce the number of component parts requiring assembly. The medical connector 10 includes an inlet housing 240, an outlet housing 250, and a gland 210. The inlet housing 240 and the outlet housing 250 may be formed from the same material to construct a single unitary housing 100. For example, each housing 240 and 250 may be formed from polycarbonate or other substantially rigid materials. The gland 210 may be formed from silicone or other elastomeric materials.

Alternatively, a single unitary connector 15 may be formed from a plurality of materials. The transition from a first material to at least a second material may not be distinct. For example, a single unitary housing 100 may consist of a substantially rigid homogeneous material in a first region (e.g., an exterior portion), and a transitioning blend of a substantially rigid material and an elastomeric material (e.g., an interior portion). A material blend may be achieved, for example, as a result of the 3D printer depositing different materials or different grades of a material at adjacent points during the 3D printing process. A transition blend refers to varying the material blend across a printed layer and/or from printed layer to printed layer (e.g., by changing the ratio of deposited material). In a similar manner, the gland 210 may consist of a transition blend of a substantially rigid material and an elastomeric material in a first region (e.g., an exterior portion) and an elastomeric material in a second region (e.g., an interior portion). The second region of the single unitary housing 100 may be formed as a unitary piece with the first region of the gland 210 to construct the single unitary connector 15.

The medical connector 10 components (e.g., the inlet housing 240, the outlet housing 250, and the gland 210) may be manufactured in a variety of ways. Illustrative embodiments of the invention manufacture the various components of the connector 10 as a unitary piece. To that end, two or more components may be formed as a single piece. For example, in some embodiments, the inlet housing 240 and the outlet housing 250 are manufactured such that they form a single unitary housing 100. In other embodiments, the inlet housing 240, the outlet housing 250 and the gland 210 are formed as a single unitary connector 15. In further embodiments, the inlet housing 240 (or the outlet housing 250) and the gland 210 are formed as a single piece. To achieve single piece structures during manufacturing, in some embodiments, the medical connector 10 may be manufactured by additive printing methods, such as 3D printing.

Figure 3:
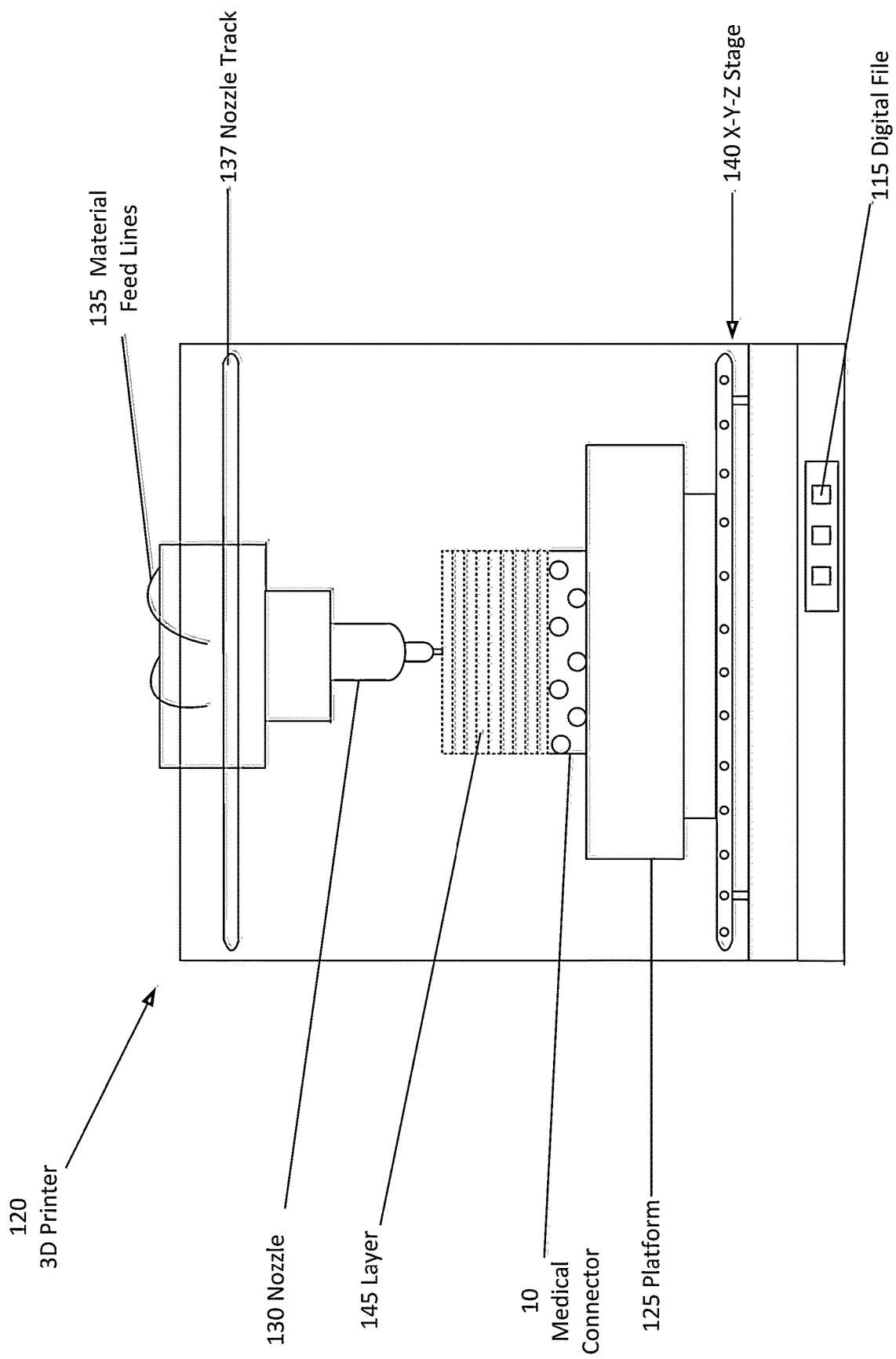
FIG. 3 schematically shows a 3D-printer printing a medical connector in accordance with illustrative embodiments of the invention.

FIG. 3 schematically shows a perspective view of a 3D printer 120 in the process of printing a medical connector 10 in accordance with illustrative embodiments of the invention. As known by those in the art, additive printing processes may form a piece from one or more materials. The 3D printing process, for example, generally begins by registering a digital file 115 of an object (in this case the connector 10) to be printed with the 3D printer 120, which may include a printing platform 125. The digital file 115 of the object may include geometric data, as well as material data as a function of geometric data. The digital file 115 allows the 3D printer 120 to print the medical connector 10 layer-by-layer 145, and adjust the type of material printed as function of geometric print location. Such 3D printing digital file 115 formats are known to those having skill in the art, for example, object ("OBJ"), stereolithography ("STL"), and computer aided design ("CAD") file formats.

The 3D printer 120 has one or more printing nozzle 130 through which material is extruded. The print nozzle(s) 130 may each have their own dedicated material feed 135. For example, one nozzle 130 may extrude polycarbonate materials and a second nozzle 130 may extrude silicone materials. By using multiple nozzles 130, a single unitary medical connector 10 may be formed from multiple materials. Although the nozzles 130 are described as printing different materials, in other embodiments, the nozzles 130 may print the same material. Alternatively or additionally, in further embodiments, the 3D printer 120 may have a single nozzle 130 with multiple dedicated material feed lines 135. In such embodiments, the nozzle 130 may alternate between the material feed lines 135 at appropriate geometric locations during printing as the digital file 115 indicates.

Although the above discussion generally describes an extrusion process of 3D printing, commonly referred to as Fused Deposition Modeling ("FDM"), it should be understood that other additive printing methods may be used to produce the unitary connector 15 and/or housing 100 described herein. For example, based on the material requirements for a particular application and/or connector 15, processes including, but not limited to, stereolithography, powder bed and inkjet head 3D printing, selective laser melting, selective heat sintering, selective laser sintering, and/or direct metal laser sintering may be used. To that end, various embodiments may use commercial additive manufacturing devices such as such as the Objet260 Connex3 made by Stratasys Ltd. (Eden Prairie, MN, USA).

Prior to starting the printing process, the user may calibrate the 3D printer 120, the print heads, and/or nozzles 130 to accurately print the appropriate material at the appropriate geometric location. As the 3D printing process begins, the nozzle 130 deposits the material and then moves in relation to the platform 125 to the next deposit location. To accomplish this movement, the 3D printing nozzle 130 may move on a track 137. The track 137 allows the 3D printing nozzle 130 to move in several dimensions, e.g., up to three-dimensions relative to the platform 125. Alternatively or additionally, the platform 125 may be mounted on an X-Y-Z stage 140. Again, the platform 125 may move in three-dimensions relative to the printing nozzle 130.

As the process continues, the 3D printer 120 will continue to form the medical connector 10 in layers 145. As shown in FIG. 3, the layers 145 are added one on top of the other until the medical connector 10 is fully printed. It should be noted that depending on the complexity of the connector 15, it may be necessary to print a support material in the layers 145 to allow the construction of overhang parts. In embodiments requiring support material, the support may be mechanically or chemically (e.g., dissolved) removed upon completion of the connector 10. The support material may be any kind of commercially available support material, including, for example, PolySupport™ by Polymaker (Shanghai, China) or a dissolvable support material, such as Dissolvable Filament made by MakerBot® Industries, LLC (New York, New York, USA).

Illustrative embodiments of the invention may 3D print various components of the connector 10 separately (e.g., the inlet housing 240, the outlet housing 250, and the gland 210 may be printed as separate pieces to be assembled). The components may be printed with a plurality of materials. For example, the gland 210 may be printed using multiple durometers of silicone that may or may not be blended (as will be discussed in further detail below). As mentioned above, in some embodiments, more than one component may be printed as a single unitary piece (e.g., unitary housing 100, unitary connector 15, etc.). As previously described, generally the housings 240 and 250 are made from a different material than the gland 210, which is deformable. Therefore, the 3D printer 120 may print the housings 240 and 250 as a single unitary housing 100 from a single material. Alternatively, the 3D printer 120 may print the housing 240 and 250 as a single unitary housing 100 from multiple materials (e.g., the inlet could be a substantially rigid material in a first region (e.g., an exterior portion) and a transition blend of a substantially rigid material and an elastomeric material in a second region (e.g., an interior portion), or vice-versa, to aid in the construction of a single unitary connector 15. The gland 210 may be printed at the same time as the unitary housing 100 (e.g., as a separate component or as a single component with the housing 100), or may be manufactured separately and added after the unitary housing 100 is completed.

Figure 4A:
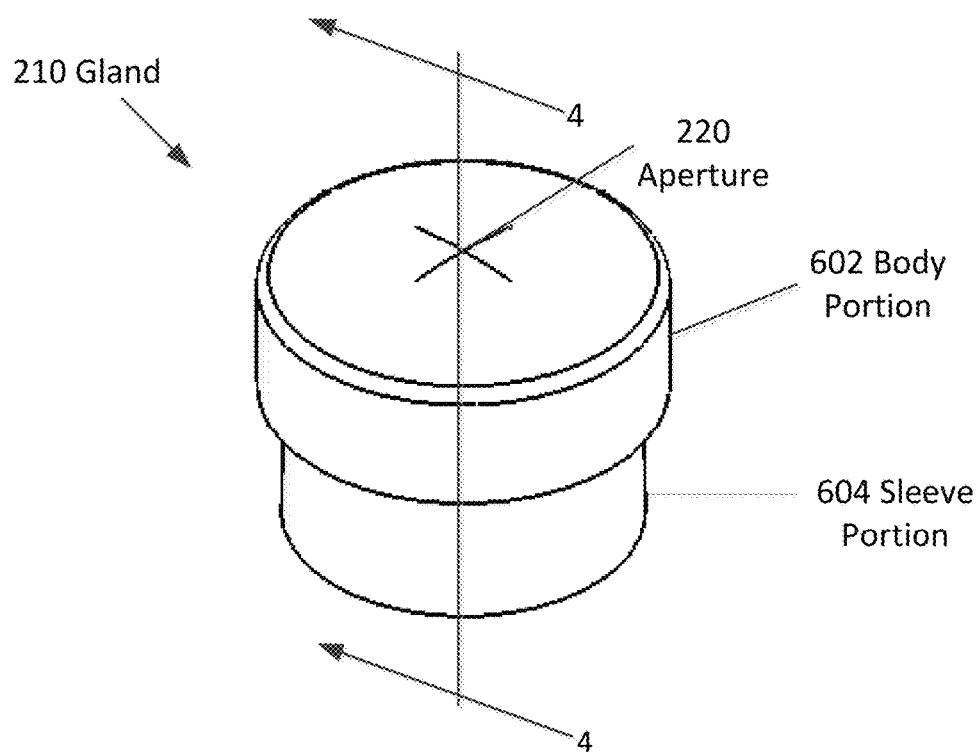
FIG. 4A schematically shows an isometric view of the gland formed in accordance with illustrative embodiments of the invention.

FIG. 4A schematically shows an isometric view of the gland 210 in accordance with illustrative embodiments of the invention. As noted above the gland 210 may be printed separately or simultaneously with the housing (e.g., in-layer 145 with inlet housing 240 and/or outlet housing 250), depending on the application, connector type and/or manufacturing desires. As shown, the resilient gland 210 has a resealable aperture 220 that extends entirely through the gland 210 (e.g., through a proximal surface of the gland 210). The printer 120 may, for example, print the aperture 220 by leaving a small amount of unprinted space. Alternatively, or additionally, the aperture 220 may be a pierced hole, or one or more slits (e.g., arranged into a cross) formed after the gland 210 is printed.

Figure 4B:
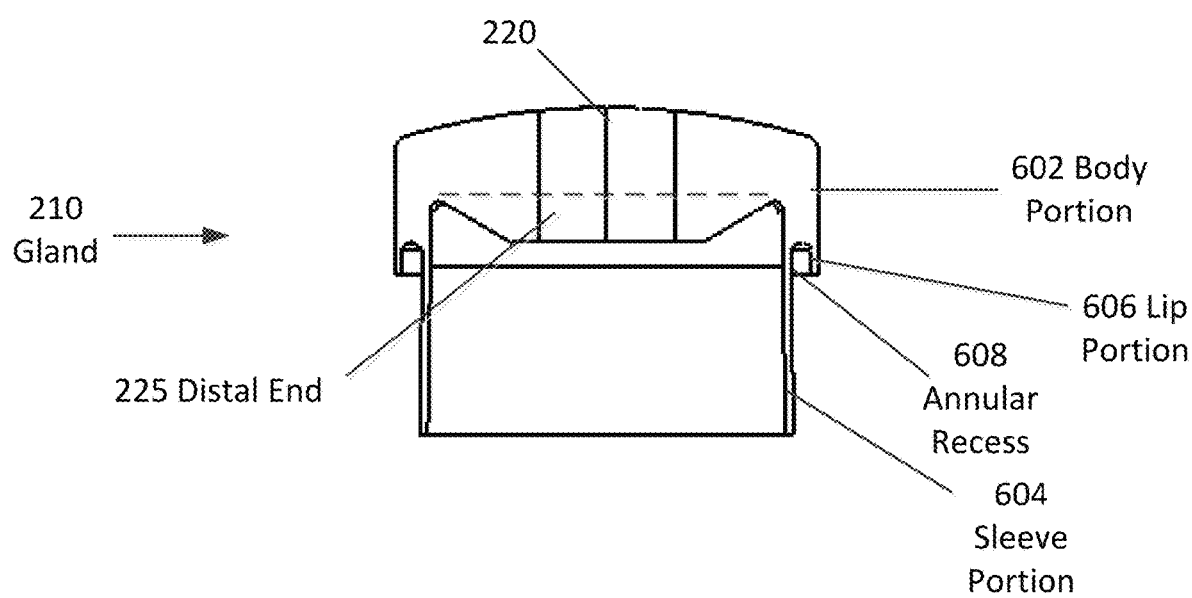
FIG. 4B schematically shows an isometric cross-sectional view of the gland shown in FIG. 4A along line 4-4.

FIG. 4B schematically shows an isometric cross-sectional view of the gland 210 shown in FIG. 4A along line 4-4. As best shown in FIGS. 4A-4B, the gland 210 may have a body portion 602 and a sleeve portion 604. The gland 210 may be printed as a single piece using one or more materials, and/or one or more grades of material. The body portion 602 may contain the aperture 220 and may (see FIG. 5A) extend above the exterior inlet face 260 of the inlet housing 240. The sleeve portion 604 may extend distally from the body portion 602 and conform to the inner diameter of the inlet housing 240. In some embodiments, the gland 210 has a lip portion 606 that conforms to the outer diameter of the inlet housing 240. In such embodiments, the lip portion 606 and the sleeve portion 604 can create an annular recess 608 configured to be printed on an exterior inlet face 260 of the inlet housing 240. The annular recess 608 increases the surface area of the gland 210, which may improve bonding (e.g., from the 3D printing) with the inlet housing 240. To that end, the gland 210 may be printed with a lower-durometer grade of silicone near the body portion 602 for ease of deformation, and higher-durometer silicone (or other material) may be printed along the sleeve portion 604.

Figure 5A:
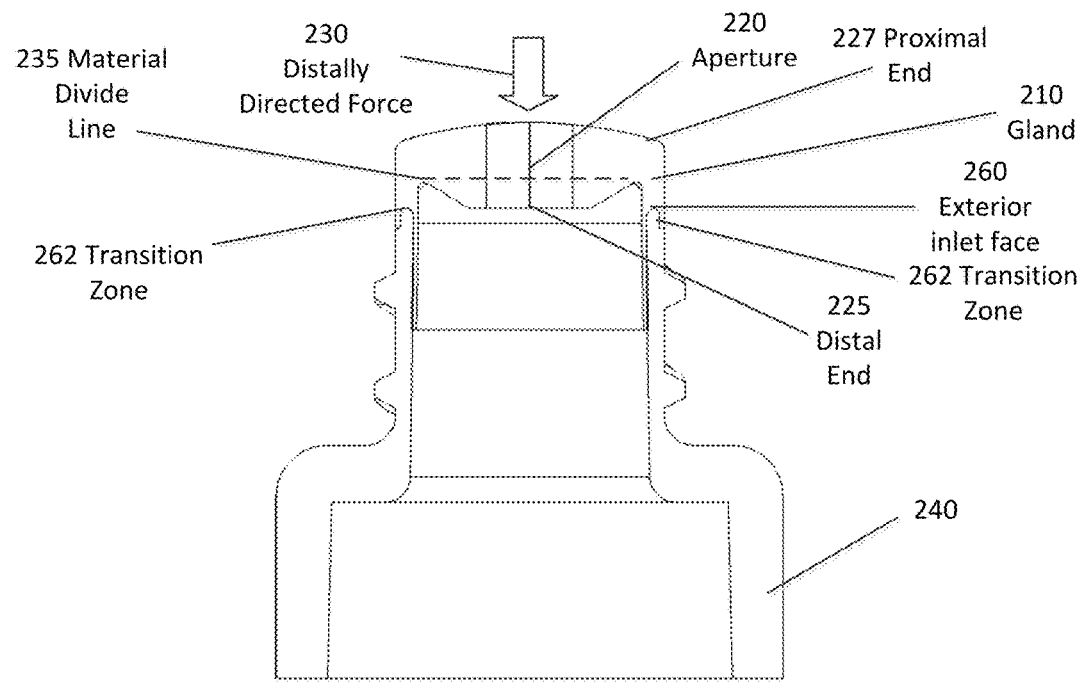
FIG. 5A schematically shows a cross-sectional view of the inlet housing formed as a single piece with the gland in FIG. 4A in a closed mode in accordance with illustrative embodiments of the invention.

FIG. 5A schematically shows a cross-sectional view of the inlet housing 240 formed as a unitary piece with the gland 210 in accordance with illustrative embodiments of the invention. Although the figure only shows the inlet housing 240 and the gland 210, it should be understood that the gland 210 may be printed with the entire single unitary housing 100. During use, the gland 210 may be exposed to a distally directed force 230, provided by, for example, a luer connector 40. The distally directed force 230 may cause the connector 10 to transition from the closed mode (shown in FIG. 5A) to the open mode (shown in FIG. 5B). For example, the gland 210 may have an activation force, i.e., an amount of force required to activate the gland 210, and open the aperture 220 to allow fluid to flow through the connector 10. This activation force may be applied via a medical instrument 40 (e.g., a luer for luer activated valves) and cause the gland 210 to move/deform and the aperture 220 to open. In some other embodiments, where the connector 10 is a pressure activated valve, the valve may have a cracking pressure applied by an air/liquid that causes the gland 210 to move/deform and the aperture 220 to open.

Although the use of two materials is discussed above, other embodiments may use more than two materials or may be formed from only a single material. Indeed, the gland 210 may be formed from a single unitary material or more than two materials (e.g., three and more). To that end, the 3D printer 120 can be loaded with the appropriate materials, and a single gland 210 may be printed from multiple materials in accordance with illustrative embodiments of the invention.

Figure 5B:
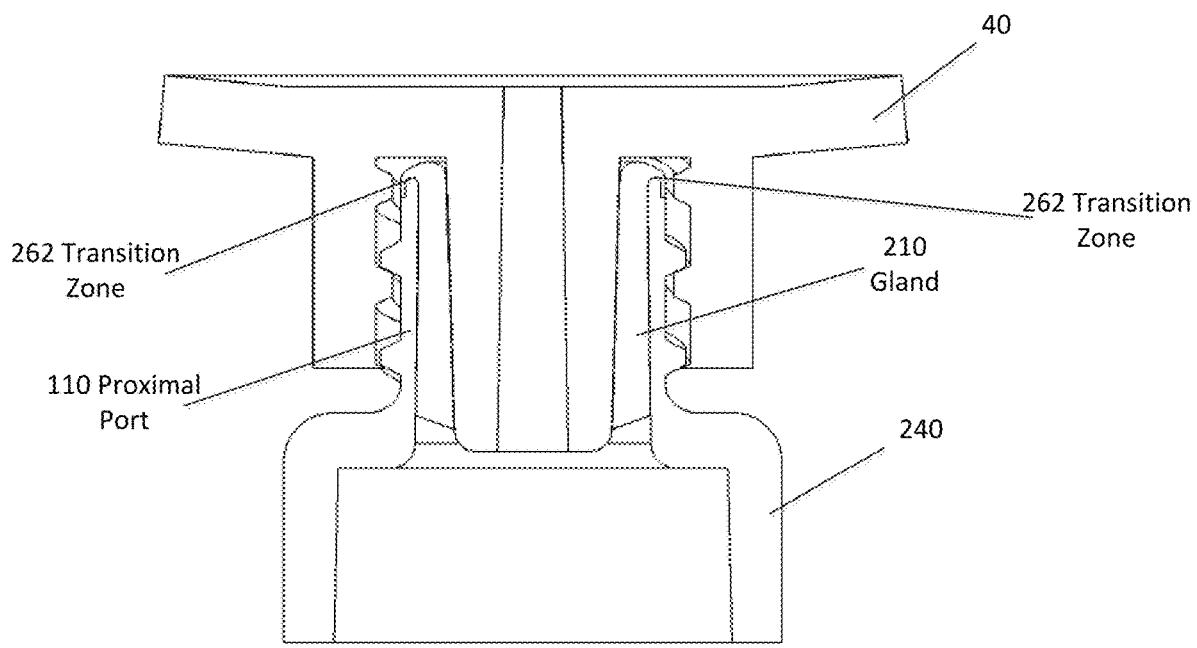
FIG. 5B schematically shows a cross-sectional view of the inlet housing shown in FIG. 5A with the gland in the open mode and an inserted medical instrument in accordance with illustrative embodiments of the invention.

FIG. 5B schematically shows a cross-sectional view of the inlet housing 240 shown in FIG. 5A with the gland 210 open (e.g., the aperture 220) and a medical instrument 40 inserted into the inlet housing 240. As mentioned above and as illustrated in FIG. 5B, a medical practitioner 20 may open the medical connector 10 by positioning the medical instrument 40 into the connector 10. In particular, when the medical instrument 40 makes contact with the raised gland 210 and the medical practitioner 20 begins to move the instrument 40 distally, the gland 210 deforms. As the medical instrument 40 is inserted further, the gland 210 deforms into the internal area of the medical connector 10 (e.g., it deforms into the area within the inlet housing 240). As the gland 210 deforms, the aperture 220 opens and allows fluid communication between the medical instrument 40 and the internal area of the housing 240. If the medical connector 10 has an internal valving mechanism (not shown), the tip of the medical instrument 40 may pass through a portion of the aperture 220 and actuate/open the internal valving mechanism.

As described above, the gland 210 may be made from a resilient material that allows the gland 210 to automatically return back to the normal (e.g., at rest) shape in the absence of pressure/force. In other words, as the medical practitioner 20 removes the medical instrument 40, the gland 210 begins to return to the at rest position shown in FIG. 5A. Additionally, as the instrument 40 is withdrawn, the aperture 220 closes, fluidly disconnecting the medical instrument 40 with the internal area of the connector 10.

It should be noted that in the embodiments shown in FIGS. 5A and 5B, because the sleeve 604 does not move with reference to the inlet housing 240, the sleeve 604 is printed with the inlet housing 240 without a support layer 265 between the sleeve 604 and the housing 240. Furthermore, the gland 210 may be printed in-layer with the housing 240. In some embodiments, the gland 210 material is printed adjacent to the housing 240 material along a transition zone 262. The transition zone 262 is the border between a first printed material and a second printed material (or more). The location of the transition zone 262 may be defined in the digital file 115. In this case, the transition zone 262 tracks the boundary between the exterior inlet face 260 and annular recess 608 shown in FIG. 4. The transition zone 262 does not have to track the boundary of traditional gland 210/housing 240 contact. For the sake of convenience, however, the transition zone 262 may be along such a boundary, and may be shown as such in the digital file 115. The transition zone 262 may be as wide or narrow as necessary, and is shown as a thin line for illustrative purposes only. In some embodiments, the transition zone 262 may be a material blending zone, as described with reference to FIG. 7.

Figure 6:
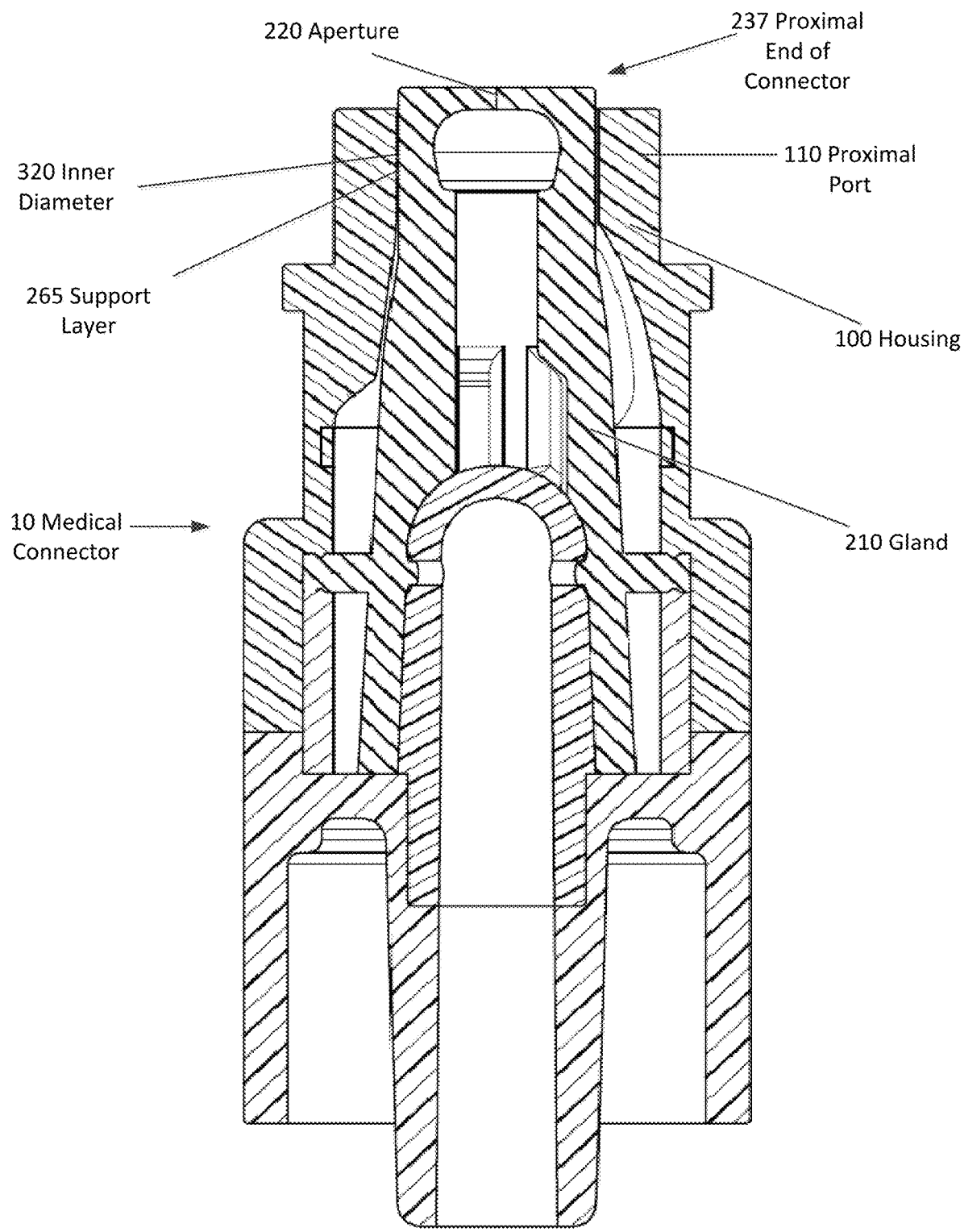
FIG. 6 schematically shows a cross-sectional view of an alternative embodiment of the medical connector formed by an additive printing process prior to coupling with a medical instrument in accordance with illustrative embodiments of the invention.

Although the embodiments shown in FIGS. 5A and 5B have a gland 210 that is at least partially unitary with the housing 240, other embodiments of the medical connector 10 may have a movable gland 210. FIG. 6 schematically shows a cross-sectional view of an alternative embodiment of a medical connector 10 formed by an additive printing process in accordance with illustrative embodiments of the invention. The connector 10 shown in FIG. 6 in many ways is similar to the connector 10 shown in FIG. 2, except as described below. Accordingly, the same reference numbers are used throughout the figures for similar and the same parts. However, it should be understood that various illustrative embodiments may operate differently, as described.

The proximal end of the gland 210 may be flush with or extend slightly above an exterior inlet face 260 of the inlet housing 12. The proximal end of the gland 210 thus presents a swabbable surface, i.e., it may be easily wiped clean with an alcohol swab, for example, or other swab. Alternatively, the proximal end of the gland 210 can be molded over the proximal port 110 to provide the swabbable surface. Such valves typically have been referred to in the art as "swabbable valves." Various other embodiments, however, may relate to other types of medical connectors 10 and thus, not all embodiments are limited to swabbable valves. In addition, some embodiments may be used with instruments having blunt tips that do not comply with the ANSI/ISO luer standard.

In the illustrative embodiment shown in FIG. 6, the connector 10 operates in a similar manner to the connector 10 shown in FIGS. 4A-5B. However, in this illustrative embodiment, the aperture 220 may be sized such that the medical instrument 40 does not penetrate the gland 210. Rather, the medical instrument 40 may deform the gland 210 enough to open the aperture 220, but not actually pass through the aperture 220. To that end, a proximal end 237 of the connector 10 has a resealable aperture 220 that extends through its entire profile. Illustrative embodiments of the gland 210 may be printed to have the aforementioned features.

As discussed, the gland 210 and the housing 100 may be 3D printed as a unitary piece. Some illustrative embodiments print the gland 210 in such a way as to allow the gland 210 to move relative to the housing 100, while still allowing the geometry of the connector 10 to force the gland 210 closed. To that end, illustrative embodiments of the invention print, during the manufacturing process, a thin support layer 265 between the housing 100 and the surface of the gland 210 that contacts the housing 100 (for example, a support layer 265 may be printed between inner diameter 320 and the gland 210). After the support layer 265 is removed, the gland 210 is able to move relative to the housing 100 because the gland 210 was printed and bonded to the now removed support layer 265 rather than the housing 100. Thus, the gland 210 remains closed as a result of internal pressure applied by the housing 100, but also movable relative to the housing 100. As mentioned above, a variety of support materials can be used. However, illustrative embodiments preferably use a dissolvable support material to ensure that all support material internal to the connector 10 is removed.

Figure 7:
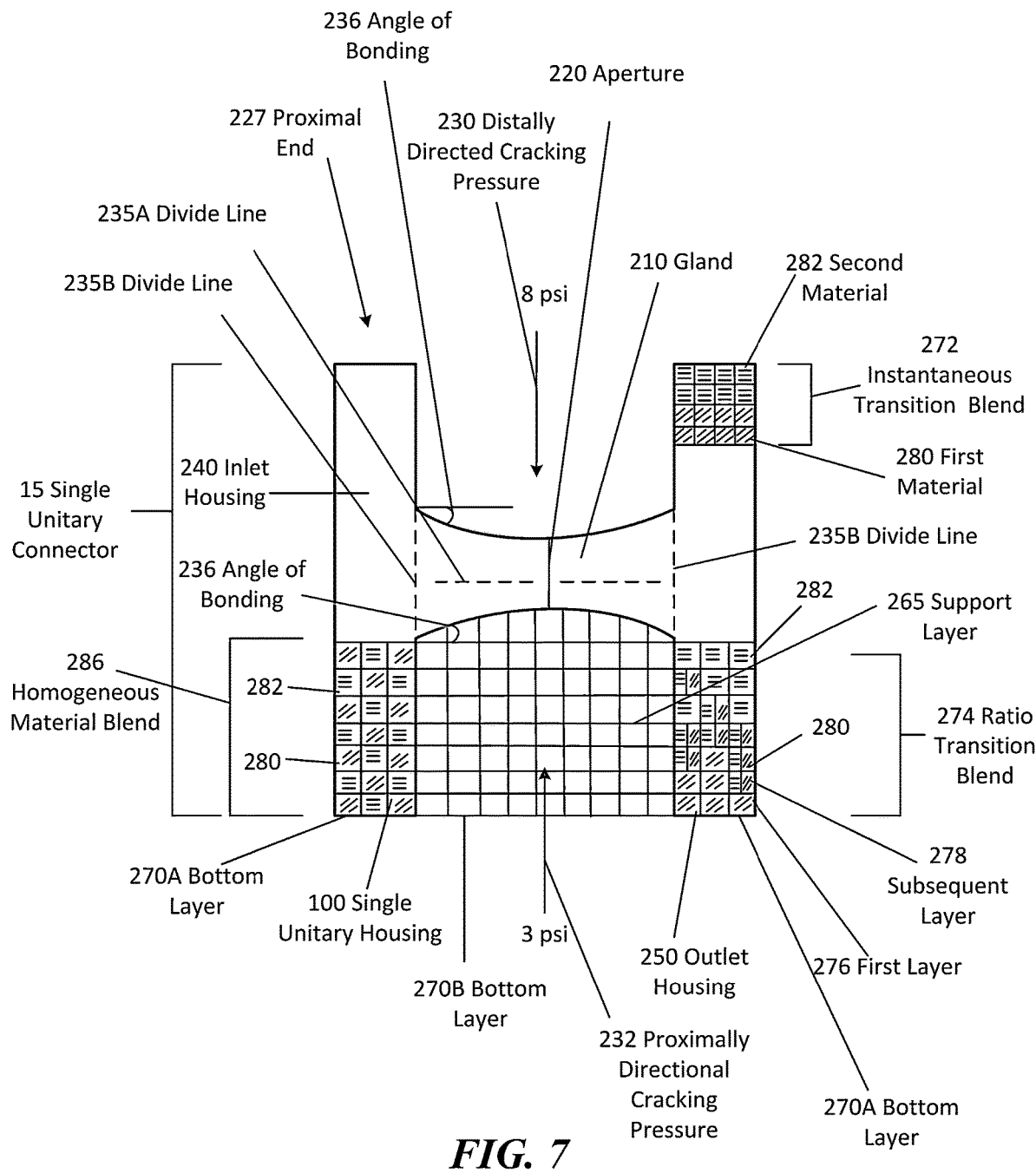
FIG. 7 schematically shows a cross-sectional view of a further alternative embodiment of the medical connector in accordance with illustrative embodiments of the invention.

FIG. 7 schematically shows a cross-sectional view of another alternative embodiment of a medical connector 10 formed by an additive printing process in accordance with illustrative embodiments of the invention. The medical connector 10 illustratively is a pressure activated valve 10. During use, the gland 210 may be exposed to a pressure that causes the connector 10 to transition from the closed mode to the open mode. For example, the gland 210 may have a cracking pressure, i.e., an amount of pressure required to activate the gland 210, and open the aperture 220 to allow fluid to flow through the connector 10. As shown, the gland 210 has a distally directed cracking pressure 230, and a proximally directed cracking pressure 232.

In some embodiments the amount of pressure required to open the connector 10 (e.g., the aperture 220) may vary depending on the direction from which the pressure is applied. For example, the gland 210 may have a distally directed cracking pressure 230 (i.e., the amount of pressure required to activate the valve when directing pressure towards the distal end 225), and a proximally directed cracking pressure 232 (i.e., the amount of pressure required to activate the connector 10 when directing pressure towards the proximal end 227). The distally directed cracking pressure 230 and the proximally directed cracking pressure 232 may not necessarily be the same. For example, in such embodiments, the distally directed cracking pressure 230 may be 5-10 pounds per square inch (e.g. 8 psi), while the proximally directed cracking pressure 232 may be 1-5 psi (e.g., 3 psi). Alternatively, the proximally directed cracking pressure 232 may be greater than the distally directed cracking pressure 230.

The cracking pressure of the gland 210 is adjustable by a number of methods. For example, the gland 210 may be formed from more than one material. As shown, the gland 210 is formed from a first material above the material divide line 235A, and a second material below the material divide line 235A. For example, the gland 210 may have a first durometer of silicone above the material divide line 235A and a second durometer of silicone below the material divide line 235A, wherein the first and second materials may or may not blend as each material approaches the material divide line 235A-B. The use of different materials and/or material blending in the gland 210 can adjust the cracking pressure of the gland 210.

Although the use of two materials is discussed above, other embodiments may use more than two materials or may be formed from only a single material. Indeed, the gland 210 may be formed from a single unitary material or more than two materials (e.g., three and more). Furthermore, the gland 210 may be formed substantially by a transitioning blend of multiple materials, wherein each layer 145 consists of a material blend ratio that is distinct from most or all of the other layers 145. For example, at least the external layer(s) forming the proximal end 227 of the gland 210 may have a material blend ratio that enhances the tear resistance of the gland 210 where it contacts the medical instrument 40. The material blend ratio of the remaining layers 145 that are formed moving towards the distal end 225 of the gland 210 transition to a material blend ratio that enhances elasticity of the gland 210 to ensure the aperture 220 is closed when the medical instrument 40 is not in contact with the gland 210. To that end, the 3D printer 120 can be loaded with the appropriate materials, and a single gland 210 may be printed from multiple materials in accordance with illustrative embodiments of the invention.

Additionally, or alternatively, the cracking pressures 230 and 232 can be modified by the amount and orientation of the material printed. For example, the amount of material printed below the material divide line 235A may be considerably less than the material printed above the material divide line 235A. Furthermore, the material below the material divide line 235A may be printed with a different architecture (e.g., angles of bonding 236 to the walls of the housing 100). The user/manufacturer may manipulate these variables as needed to achieve the desired proximally and distally directed cracking pressures 232 and 230. Although the above discussion has referred to material divide line 235A, it should be understood that the same principles apply to material divide line 235B. Furthermore, the orientations of material divide lines 235A and 235B are merely exemplary, and material divide lines can take any orientation (and do not have to be linear lines).

In the depicted illustrative embodiment, the gland 210 is printed simultaneously with the single unitary housing 100 (comprising inlet housing 240 and outlet housing 250) to form a single unitary connector 15. For the convenience of the reader, material divide lines 235A and 235B are shown. It should be understood that material divide lines 235A and 235B can take other configurations (e.g., as indicated in the digital file 115), and are not limited to the configurations shown herein. When the printing process forms the single unitary connector 15, it is generally printed in layers 145. If the connector 10 is printed in the upright position depicted, for example, the bottom layer 270A is printed first. The bottom layer 270B of the support layers 265 may also be printed simultaneously with the bottom layer 270A of the connector 10. The 3D printer 120 may print the material bottom layer 270A first, and then print the support bottom layer 270B, or it may alternate between connector 10 material and support layer 265 material during the printing process. However, some illustrative embodiments use materials and/or dimensions that do not require support layers 265.

Once the printing process reaches material divide line 235B, the printing process may, for example, print, in a single layer 145, portions of the housing 100, support layer 265, and gland 210. Furthermore, the gland 210 may be formed from more than one material. For example, the material divide line 235A is a location at which the gland 210 starts to be printed from a second material. The materials used to print the gland 210 may vary in hardness and density, as well as other properties. The 3D printer 120 continues to print the connector 10 as described in the digital file 115. The connector 10 may not require any support layers 265 above the gland 210, as there are no unsupported overhangs over the gland 210. To prevent the aperture 220 from sealing on itself, a thin layer of support material 264 may be printed between the gland 210 material. Alternatively, or additionally, the aperture 220 may be created after printing.

The material divide lines 235A and 235B are simplified illustrations of material blending. The material divide lines 235A and 235B indicate that the printing process may have an instantaneous transition from a first material to a second material (and third material, etc.). However, illustrative embodiments of the invention may use a variety and/or combination of material blends when forming unitary components (such as single unitary connector 15).

One example of a material blend is an instantaneous transition blend 272. As the printer 120 prints layer-by-layer 145, it may print a first material 280 on one layer 145 and then print a second material 282 on top of the first material 280. The blend transition is referred to as "instantaneous" because the printed material switches entirely from one layer 145 to the next, without any transition layers. The material divide lines 235A and 235B are also considered to be instantaneous transition blend 272. It should be understood that while the transition is referred to as instantaneous, there may be intermingling between the first material 280 and the second material 282 at the micro-level (e.g., although the layer 145 is roughly smooth to the naked eye, may be textured under a microscope). Furthermore, some parts of two adjacent layers may have an instantaneous transition, while others may not.

Another type of material blend is a ratio transition blend 274. As seen, material is deposited in such a way that a first layer 276 is printed of a large ratio (or entirely) of the first material 280 compared to the second material 282, and the subsequent layer 278 is printed with a smaller ratio of a first material 280 compared to the second material 282. This can continue on a layer-by-layer basis until the material being printed has transitioned entirely from the first material 280 to the second material 282. It should be understood that the ratio transition blend 274 can take place with a plurality of different materials (e.g., two or more) and occur over two or more layers 145.

Another example of a blend used in accordance with illustrative embodiments of the invention is a homogeneous material blend 286. The homogeneous material blend 286 describes a blend of a plurality of materials (e.g., a first material 280 and a second material 282). Unlike the instantaneous transition blend 272 or the ratio transition blend 276, the homogeneous blend 286 does not necessarily transition from a layer 145 comprising a majority of the first material 280 to a layer 145 comprising a majority of the second material 282. Instead, the first material 280 and the second material 282 are dispersed amongst each other in different ratios. As shown, a checkerboard pattern is formed by the homogeneous material blend 286. This is but one example of a homogeneous material blend 286. Homogeneous material blends 286 can be accomplished by printing different material point-by-point in the layer 145, down to the finest print resolution allowed by the 3D printer. As shown, the ratio of first material 280 to second material 282 is roughly 1:1. However, the ratio of the first material 280 to the second material 282 could be any ratio (e.g., 3:1, 4:1, etc.).

Alternatively, or additionally, the homogeneous material blend 286 may be produced by mixing the first material 280 and the second material 282 together. In other words, the two materials 280 and 282 can be mixed and fed through a single material feed line 135. Accordingly, a single material feed line 135 is able to print the homogeneous blend 286 without having to alternate between material feed lines 135. This may also allow for a homogeneous blend 286 with a much finer resolution than that provided by the 3D printer 120 printing the materials point-by-point. Additionally, a material mixture may allow for increased printing speed. In some embodiments, the single unitary connector 15 and/or the single unitary housing 100 may be formed entirely from a homogeneous material blend 286. A person of skill in the art understands that a mixed homogeneous material blend 286 may have different material ratios from print point to print point (although, in theory, they should be roughly the same depending on the amount of mixing and material properties).

Although the materials are referred to as the first material 280 and the second material 282, it should be understood that different grades of the same material may be used in addition, or alternatively, to different materials. Also, it should be understood that various components may be printed with a single style of blending or with many styles of blending. A person having skill in the art can imagine variations of the blending disclosed herein that still fall within the spirit of the invention. For example, different ratios of materials may be used and/or different styles of blending may be used in three dimensions depending on structural requirements of the connector 15. To that end, the digital file 115 may be analyzed using finite element analysis. Accordingly, different material blends may be created to facilitate structural requirements. For example, the connector 15 may have multiple blending zones to facilitate the formation of anchoring columns (not shown) that provide stiffness in a single direction. Furthermore, material blends can be used to enhance user convenience. For example, a homogeneous transparent material can be used to allow a nurse 20 to see fluid flow through the valve during use, and the transparent material may then have an instantaneous layer transition 272 or ratio transition blend 274 to a structurally stronger material.

FIG. 7 merely shows a single cross-section of the valve. Various cross-sections and layers 145 may use different styles of blending, and/or some cross-sections and layers 145 may use no blending at all. Additionally, although described using two materials for simplicity, any number of materials (e.g., three or more) may be blended in the above described manner.

Although some of the figures show specific connector 10 and gland 210 structure, those skilled in the art may use any of a variety of different connectors 10 (e.g., including valving mechanisms). For example, the valve mechanism may include a moveable post member (not shown) having a lumen as a part of the flow path. This post may have a solid wall surrounding and defining the lumen, and the lumen may have an opening to the interior of the housing 100. An example of a valve having this type of valve mechanism is taught by U.S. Pat. No. 6,039,302, the disclosure of which is incorporated herein, in its entirety, by reference. Of course, other valve mechanisms may include a stationary post configured other ways. Those skilled in the art can select the appropriate valve mechanism.

Figure 8:
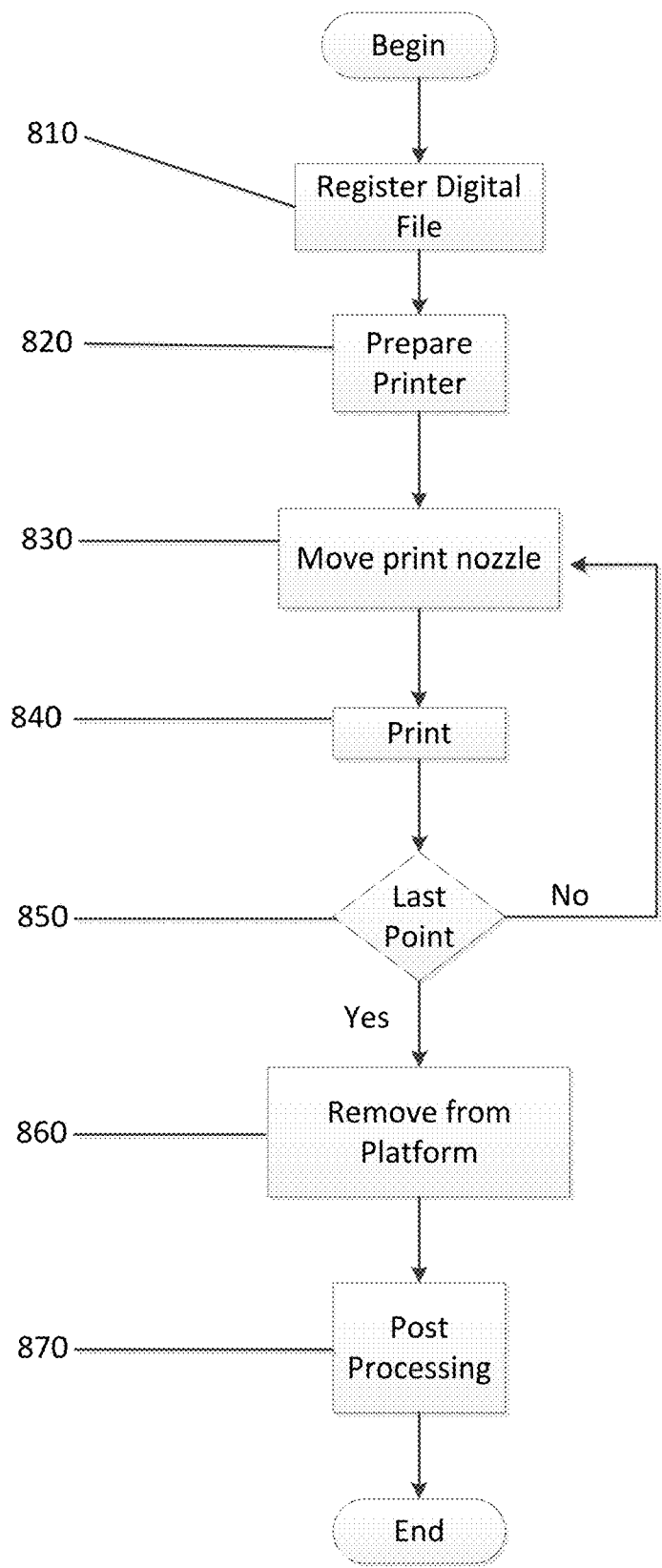
FIG. 8 shows a process of printing the medical connector in accordance with illustrative embodiments of the invention.

FIG. 8 shows a process of printing a medical connector 10 in accordance with illustrative embodiments of the invention. The process begins by registering the digital file 115 to a 3D printer 120 (step 810). Of course, to register the digital file 115 with the printer 120, the digital file 115 must be in existence. The connector 10 to be printed has an associated 3-D model developed using, for example, CAD software. The CAD file has the geometric boundaries of the connector 10, and may contain data regarding the materials used in various geometric coordinates. Alternatively, the material data may be in another digital file 115 that is incorporated in the 3D printing file. The CAD drawing is then converted to a 3D printing format, such as STL, or other 3D printer compatible format. The STL file holds data (including a list of XYZ coordinates of the connector) to produce the connector 10.

After the 3D digital file 115 is in an appropriate format, it may be registered with the computer that controls the 3D printer 120. The size and orientation of the connector 10 to be printed can be determined at that time. In some embodiments, the 3D printing software has logic that automatically calculates and includes support material into the print file. This software may be referred to as "slicing software," which tells the printer 120 how to print the connector 10. The slicing software (e.g., MakerWare by MakerBot) instructs the printer 120 on the number of layers 145 needed and the starting position. After the digital file 115 is registered, the 3D printer 120 is prepared for printing the object (step 820). The appropriate material feed lines 135 are attached and/or refilled with polymers for printing. Support material feed lines 135 are also included, as well as binders and any other consumables the printer 120 may use. Homogeneous polymers may be mixed and also loaded into a dedicated material feed line 135 at this time. At this time, the operator may wish to calibrate the 3D printer 120 prior to printing. In some embodiments, the operator may wish to add and/or revise the support material calculated by the 3D printing software.

When the printer 120 is ready to begin fabricating the connector 10, the print nozzle 130 is moved into position (step 830). It should be understood that in some additive printing processes, there may be multiple print nozzles 130. In such a case, all of the nozzles 130 are moved into position. The digital file 115 contains data indicating what type of material and/or what material feed line 135 to print from. The appropriate material is selected, and the first point is printed (step 840).

The process then checks to see whether the printed point was the last point to be printed. If that was not the last point, the process returns to step 830, and moves the print nozzle 130 into the next point to be printed. Again, the next point has associated material data. The digital file 115 indicates the material to be printed, and the 3D printer 120 prints the next point (step 840). This process continues in two-dimensions until the first layer 145 (including support material, if any) is printed. Depending on the complexity of the connector 10, and the resolution and speed of the printer 120, the printing process could take between minutes and several hours.

The digital file 115 contains data for all the layers 145 of the connector 10. After the first layer 145 is printed, the print nozzle 130 is moved into position to begin printing the next layer 145. The process continues layer-by-layer 145 until the last point is reached (step 850). After the last point of the digital file 115 is printed, the connector 10 may be removed from the platform 125 (step 860). The connector 10 may then undergo any necessary post-processing (step 870). For example, the operator or an automated machine may remove any support material from the connector 10. Alternatively, or additionally, the connector 10 may be rinsed to remove soluble support material as described above. For example, the connector 10 may be rinsed in water to remove water soluble filaments such as those made by 3D Systems, Inc.

Although the above discussion discloses various exemplary embodiments of the invention, it should be apparent that those skilled in the art can make various modifications that will achieve some of the advantages of the invention without departing from the true scope of the invention.

What is claimed is:

1. A method for producing a one-piece medical connector, the method comprising:
    depositing a first material and at least a second material through additive manufacturing to form a unitary body having rigid material properties, resilient material properties, and semi-rigid material properties;
    the medical connector comprising:
        a rigid portion forming a housing, and
        a resilient portion located at least partially within the housing, at least a movable portion of the resilient portion is configured to move relative to the rigid portion to selectively permit fluid flow through the medical connector,
        the rigid portion and the resilient portion forming a single piece.

2. A method according to claim 1, wherein the rigid portion is formed from at least the first material and the resilient portion is formed from at least the second material.

3. A method according to claim 1, wherein the medical connector further includes a transition zone located between the rigid portion and the resilient portion.

4. A method according to claim 3, wherein the transition zone is formed of a material blend of at least the first and second material and has material properties that are distinct from the rigid and resilient portions.

5. A method according to claim 4, wherein the transition zone has at least semi-rigid material properties.

6. A method according to claim 4, wherein the material blend is a homogenous material blend.

7. A method according to claim 4, wherein the material blend if a ratio transition blend.

8. A method according to claim 4, wherein the material blend is an instantaneous transition blend.

9. A method according to claim 1, wherein additive manufacturing includes at least one selected from the group consisting of 3D printing, Fused Deposition Modeling, stereolithography, powder bed and inkjet head 3D printing, selective laser melting, selective heat sintering, selective laser sintering, and direct metal laser sintering.

10. A method for producing a one-piece medical connector, the method comprising:
    depositing, using an additive manufacturing process, a plurality of first layers of a first material;
    depositing, using an additive manufacturing process, at least one transition layer formed of a material blend of at least the first material and a second material; and
    depositing, using an additive manufacturing process, a plurality of second layers of the second material, the plurality of first layers, the at least one transition layer, and the plurality of second layers forming a unitary body of the one-piece medical connector.

11. A method according to claim 10, wherein the medical connector includes:
    a rigid portion forming a housing of the medical connector; and
    a resilient portion located at least partially within the housing, at least a moveable portion of the resilient portion configured to move relative to the rigid portion to selectively permit fluid flow through the medical connector.

12. A method according to claim 11, wherein the plurality of first layers of the first material form the rigid portion and the plurality of second layers of the second material form the resilient portion.

13. A method according to claim 12, wherein the medical connector further includes a transition zone located between the rigid and resilient portions, the at least one transition layer forming the transition zone.

14. A method according to claim 13, wherein the transition zone has material properties that are distinct from the rigid and resilient portion.

15. A method according to claim 14, wherein the transition zone is at least semi-rigid.

16. A method according to claim 10, wherein additive manufacturing process includes at least one selected from the group consisting of 3D printing, Fused Deposition Modeling, stereolithography, powder bed and inkjet head 3D printing, selective laser melting, selective heat sintering, selective laser sintering, and direct metal laser sintering.

17. A method according to claim 10, wherein the material blend is a homogenous material blend.

18. A method according to claim 10, wherein the material blend if a ratio transition blend.

19. A method according to claim 10, wherein the material blend is an instantaneous transition blend.

* * * * *